United States Patent [19]
Chmel et al.

[11] Patent Number: 5,469,908
[45] Date of Patent: Nov. 28, 1995

[54] CAP FOR INVESTMENT MOLDS FOR PRECISION CASTING

[75] Inventors: James Chmel, Fav Claire, Wis.; Robert P. Berger, Encino, Calif.

[73] Assignee: Belle de St. Claire, Chatsworth, Calif.

[21] Appl. No.: 213,163

[22] Filed: Mar. 15, 1994

[51] Int. Cl.⁶ .............................. A61C 13/20; B22C 7/02; B22C 21/00
[52] U.S. Cl. .......................... 164/376; 164/237; 164/239; 249/54; 249/105
[58] Field of Search ..................................... 164/376, 237, 164/238, 239, 240; 249/54, 61, 62, 105; 220/86.1, 601

[56] References Cited

U.S. PATENT DOCUMENTS

| | | | |
|---|---|---|---|
| 1,225,206 | 5/1917 | Atkinson | 164/376 |
| 1,369,182 | 2/1921 | Moore | 164/376 |
| 1,458,835 | 6/1923 | Lynn | 164/238 |
| 1,499,132 | 6/1924 | VanHorn | 164/376 X |
| 4,962,909 | 10/1990 | Kohler | 164/376 X |
| 5,318,093 | 6/1994 | MacDonald | 164/376 X |

*Primary Examiner*—J. Reed Batten, Jr.
*Attorney, Agent, or Firm*—Notaro & Michalos

[57] ABSTRACT

A cap for an investment vessel for receiving investment material comprises a platform having a contoured edge and an underside. A wedge is located on the underside of the platform and is frictionally engageable with at least a portion of an inner edge of the top of the vessel. When the cap is placed in frictional engagement with the vessel, the contoured edge provides a restricted opening to the vessel for controlling the flow of the investment material. A lip is provided on the platform at the contoured edge for channeling investment material to the opening.

19 Claims, 4 Drawing Sheets

CAP FOR INVESTMENT MOLDS FOR PRECISION CASTING

FIELD AND BACKGROUND OF THE INVENTION

The present invention relates, in general, to casting devices for making investment molds and, more particularly, to a new and useful cap for vessels used in making investment molds for precision casting of dental prosthesis and a method for making investment molds using the cap.

Investment casting, also known as precision casting, or the lost wax casting technique, is used in dental practice to create a casting from a wax pattern that is a duplicate of the object to be cast. The wax pattern is an acurate replica of the shape of a metal or glass dental restoration such as a gold crown, partial denture framework, or metal coping for a porcelain-fused-to metal crown. The wax pattern is attached to a second piece of wax or plastic known as a sprue.

The sprue is attached to a conical sprue former in a base to hold the wax pattern in place. A casing is then placed around the wax pattern and attached to the base to form a vessel or container into which an investment solution is poured. The investment material then hardens around the wax patterns to form the "investment mold". Removal of the base leaves a conical shape in the investment mold which will direct molten metal into the investment mold. The wax, and, if present, plastic is first removed from the mold space by placing the investment mold into an oven to melt and burn out the wax and plastic.

In many known casting mold devices, a metal or plastic casing is force fit into a groove in the base to form the vessel for holding or receiving the investment solution.

The casing may be a circular ring which fits into a circular base or the casing may be an oblong so-called oval-shaped oval which fits into an oblong or oval-shaped base to form the vessel.

Investment molds or metal rings used for investing are normally filled with an investment material by two known methods. In the first method, commonly known as "investing under vacuum", the entire mold is placed in a vacuum environment as the investment material is poured into the mold. This method utilizes intricate equipment for investing under vacuum which is often subject to breakdown; and therefore, it is very easy to create molds that have bubbles and nodules. A nodule is similar to a bubble in size and configuration. The major difference is that bubbles are perfectly round whereas nodules have sharp or irregular projections generating from the surfaces of the casting.

Bubbles are caused by the entrapment of air in the investment material. Nodules are caused by openings in the surface of the investment material where it contacts the surface of the pattern. When the wax is burned out and the mold is filled with liquid metal, the metal penetrates these slight openings in the investment surface and create nodules of solid cast alloy.

Accordingly, nodules and bubbles must be removed from the surface of the casting. This is a time consuming operation involving machining; and could possibly cause damage to the casting during the machining operation.

The research literature states that mixing investment under vacuum and "Static pouring", the investment into the mold produces the least amount of bubbles when compared with alternate techniques.

The second method of investing is "static investing". Static investing involves mixing the investment material under vacuum, releasing the vacuum and pouring the investment material without vacuum into the mold until the patterns within the mold are covered with the investment material.

When static poured, small bubbles within the investment material collect on the outer surfaces of the pattern. Frequently, air is trapped in the bottom of the wax patterns which has a detrimental effect on the process. The trapped air causes the patterns to be cast with the reproduction of the trapped air becoming solid cast alloy after molten metal has been poured into the void left by the bubble within the pattern.

After the investment has been heated in a furnace to eliminate the wax pattern, molten metal will be poured into the void mold to reproduce the wax pattern in solid metal. The molten metal will fill all voids including all areas where air has been trapped, thus all bubbles or voids on, in, or attached to the pattern will be replicated in solid metal.

For any investment method, it is critical that the intersurface of the pattern fit the patient's tooth. This may not occur if bubbles are encapsulated in the investment material because they will adhere to all of the pattern surfaces that the investment contacts.

FIG. 1 illustrates the most common method of making an investment mold in which the investment material 4 is poured into the mold 10 while in a vertical position. It is well-known that there is a tendency for air to be trapped in the bottom of the copings at 6 since the investment material has a tendency to flow over the top of each coping 7 before the air can escape.

In an effort to prevent this problem, a small sable brush is used to pick up small amounts of the investment material 4 in the mold and place the investment on the side wall of each coping pattern. The mold is then vibrated in order to permit the investment material to flow to the bottom of the pattern in order to displace the air in the bottom of the mold prior to filling the balance of the coping.

However, two major difficulties are encountered when using the brush. First, the bristles of the brush must be wet in order to bring them to a point for facilitating the handling of the investment material. The brush is simply dipped in water and shaken a couple of times in an effort to remove the excess water. The investment material is then picked up on the brush and placed on the wax coping. Accordingly, the water contained within the bristles of the brush mixes with the investment material thereby diluting it. This causes a variance in the expansion of the investment material placed inside of each coping pattern. Thus, a variance in the fit of the casting is created which causes misfits and may sometimes require the fabrication of another casting.

It is rare that another casting would have to be made, however, under expanded castings require excess machining in order to make the casting fit the plaster replica of the patients tooth and subsequently the patient's tooth.

The second difficulty encountered when using a brush is that there is always air contained within the bristles of the brush is deposited in the form of small bubbles inside of the coping at the time of investing. These bubbles create a misfit, if left unattended. Accordingly, the bubbles must be removed from the surface of the casting which proves to be very time consuming.

Furthermore, the average working time for investment material is roughly six minutes. Thus, when employing any of the known investment methods, it is difficult to achieve the filling of multiple molds prior to the investment material setting.

SUMMARY OF THE INVENTION

The present invention is a cap for an investment mold vessel which allows the vessel to be filled with investment material while in a horizontal position. The investment cap is frictionally engageable with an open top of the molding vessel. This allows the the mold to be invested in a horizontal position. The mixed investment material is poured into a restricted inlet in the cap so that the material is channeled along the underside of the cap to the side wall of the mold vessel.

The reduced opening of the cap prevents excess investment material from being forced into the mold. The mold is vibrated while the investment material is poured into the cap's restricted opening which ensures that the mold is filled at a sufficient rate which will not entrap air bubbles in the investment material while inside the vessel.

By orienting the mold vessel in a horizontal position prior to filling, the side wall of each coping pattern is filled first followed by filling along the occlusal surface of each pattern and finally, filling the other side wall.

It is an object of the present invention to provide a cap for an investment vessel which permits the horizontal filling of the vessel with investment material.

It is another object of the present invention to provide a cap for an investment vessel which eliminates investing under vacuum or static investing methods.

It is another object of the present invention to provide a cap for an investment vessel which produces castings with extremely low incidence of incapsulated bubbles or nodules.

It is another object of the present invention to provide a cap for an investment vessel which allows numerous molds to be filled with a single mix of investment material.

It is another object of the present invention to allow the investor to visually see the inside surfaces of each pattern, to prevent encapsulation of air, during the filling of the mold with investment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which multiple embodiments of the invention are illustrated.

DESCRIPTION OF THE PREFERRED EMBODIMENTS

The present invention pertains to the filling of investment mold vessels with an investment material. The present invention comprises both a cap used in conjunction with an investment vessel and a method of filling the vessel using the cap.

Figure 4:
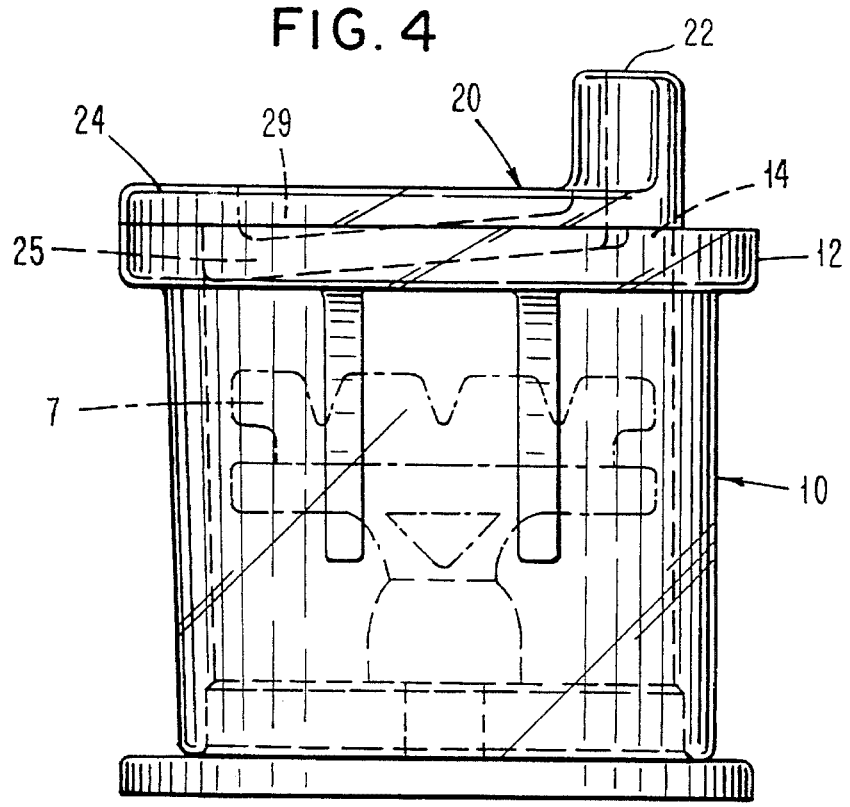
FIG. 4 is a view illustrating a cap according to the present invention used in conjunction with an investment mold.

The same reference numerals are used to designate the same or similar features. Referring to the drawings, particularly FIG. 4, the present invention comprises a cap 20 used in conjunction with an investment vessel or mold 10 containing a form such as a plurality of copings 7, indicated by phantom lines, commonly used in lost wax methods.

As shown in FIGS. 4–8, the cap 20 comprises a platform 24 which is seated on the upper edge of the top of mold 10, for instance, on flange 12 as depicted in FIG. 4. Cap 20 is made of a flexible plastic material, preferably polyvinyl chloride, and is transparent for allowing viewing of the contents of the mold 10.

Figure 7:
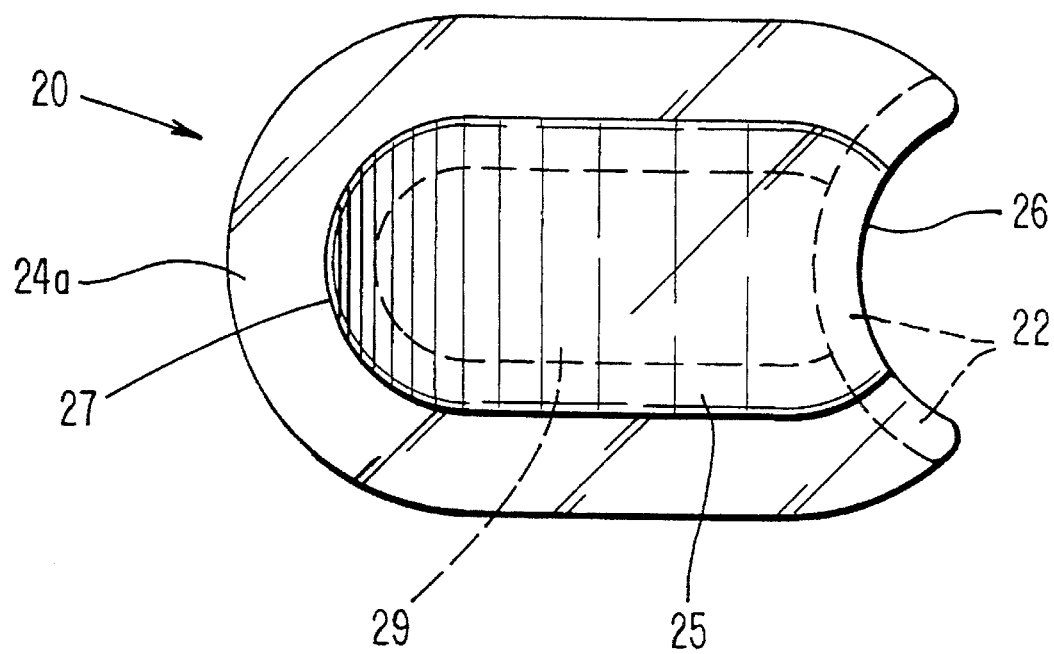
FIG. 7 is a bottom view of the cap of FIG. 4.
Figure 8:
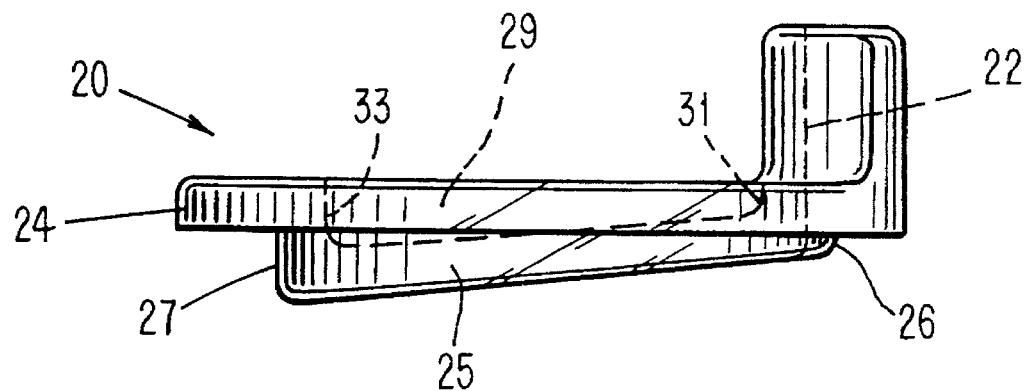
FIG. 8 is an elevational side view of the cap of FIG. 4.

FIG. 7 shows the cap 20 having a heel or wedge 25 located at underside 24a of the platform 24. Wedge 25 is a raised inclined portion extending outwardly from underside 24a and has a front wall 26 and a rear wall 27. Rear wall 27 is larger than the front wall 26 providing an inclined inner surface for the wedge 25 as shown in FIG. 8.

Wedge 25 is frictionally engageable with the upper edge of the mold 10 at flange 12 for allowing the cap 20 to be frictionally held against the upper edge of mold 10. Wedge 25 provides a channeling surface for the investment material 4.

Figure 1:
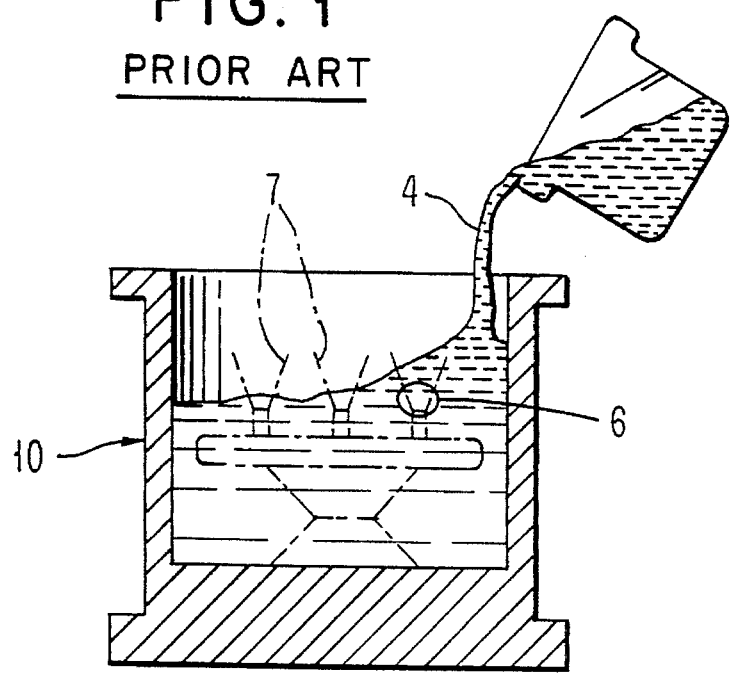
FIG. 1 is a schematic view illustrating a known method for filling an investment mold.
Figure 2:
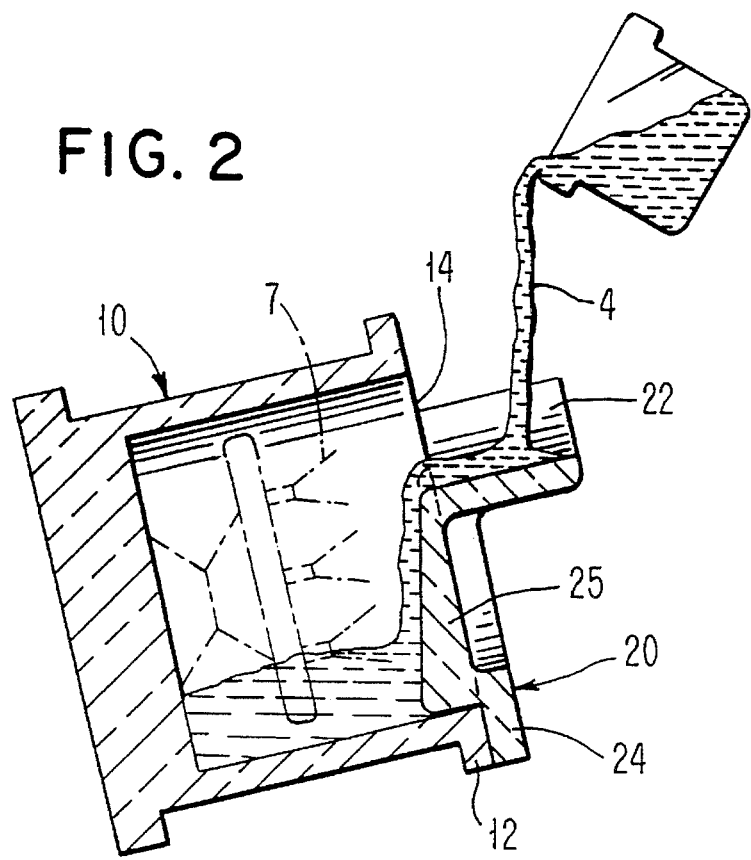
FIG. 2 is a schematic view illustrating the present invention.
Figure 3:
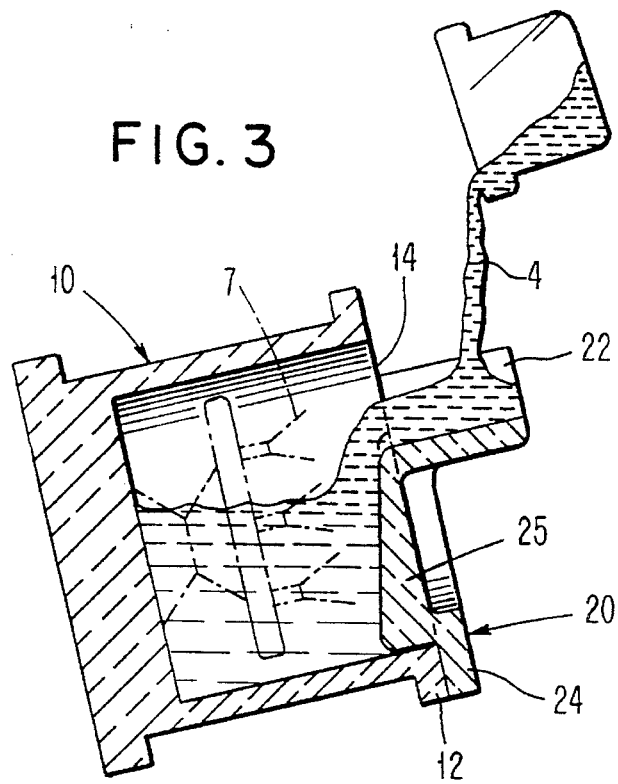
FIG. 3 is a schematic view further illustrating the present invention.

The wedge 25 frictionally engages at least a portion of the upper edge of mold 10 and rear wall 27 contacts the side wall of the mold 10, as shown in FIGS. 2 and 3, so that investment material 4 flows directly to the side wall of mold 10 after being channeled over the inclined surface of the wedge 25.

Figure 5:
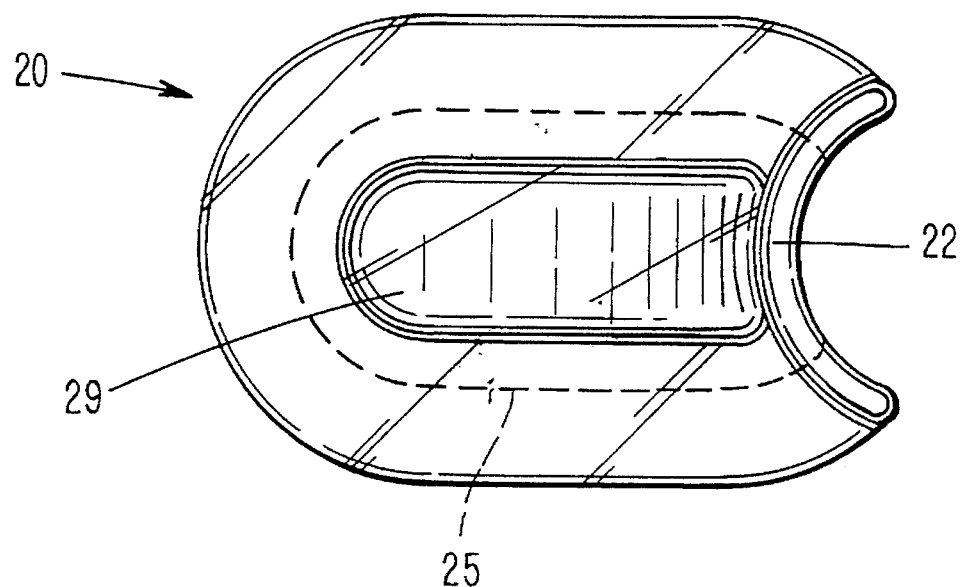
FIG. 5 is a top view of the cap of FIG. 4.
Figure 6:
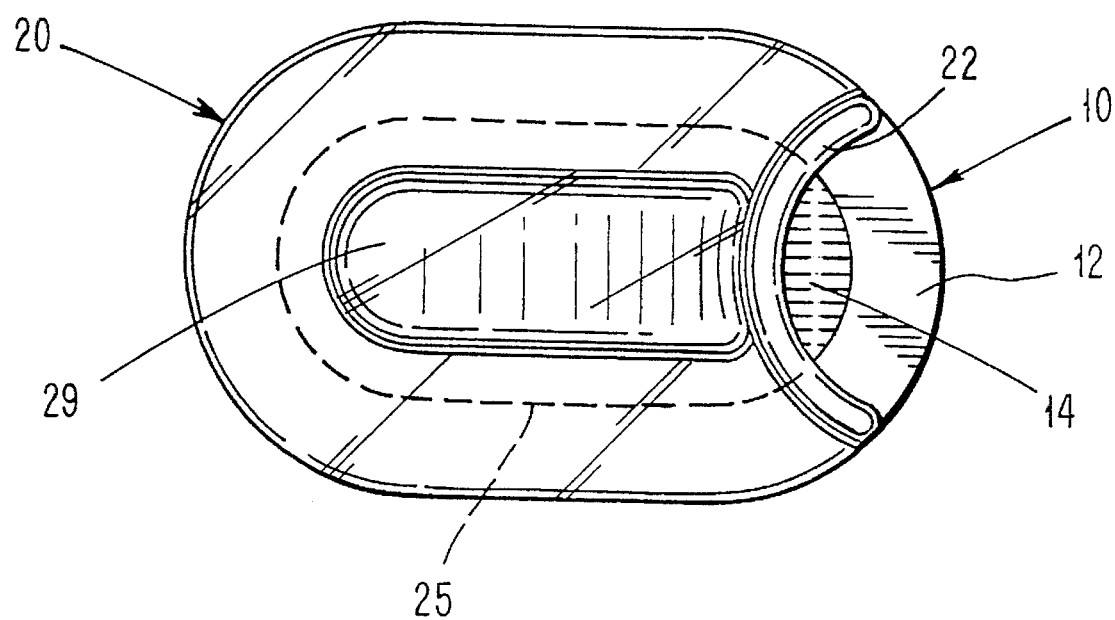
FIG. 6 is a top view of FIG. 4.

As shown in FIGS. 5–7, cap 20 has a contoured or notched edge for creating opening 14 when placed in frictional engagement with the mold 10 as illustrated in FIG. 6. Opening 14 is a restricted opening which regulates the flow of investment material 4 into the mold 10 for significantly reducing the presence of bubbles.

FIG. 8 shows a lip 22 outwardly extending from the platform 24 at the contoured edge of the platform 24 and front wall 26 of wedge 25. Lip 22 provies a catch or platform for the investment material 4 to be poured onto when cap 20 is placed over the top of vessel 10 so that investment material 4 can be channeld through opening 14 into mold 10 as shown in FIGS. 2 and 3.

As illustrated in FIGS. 5–7, the contoured edge of platform 24 and the front end 26 of wedge 25 and the lip 22 have a semi-circular shape. However, these features are not limited to this shape and may include a V-shape or other suitable shape for channeling investment material 4 into the opening 14. The cap 20 along with wedge 25 have a substantially oblong shape, however, any suitable type shape can be used for capping the mold 10.

FIG. 8 also shows the platform 24 and the wedge 25 having a depression 29 cut therein for facilitating handling by a user. Depression 29 has a front wall 31 and rear wall 33. Rear wall 33 is at a greater depth than front wall 31 which creates a floor in the depression 29 which is an inclined surface.

FIGS. 2 and 3 illustrate a method according to the present invention for filling the mold 10 with investment material 4 which includes frictionally engaging cap 20 with the top edge of mold 10; and horizontally positioning mold 10 such that investment material 4 can be poured onto lip 22 for channeling the material 4 through opening 14 along wedge 25 to the side wall of mold 10. By horizontal, the vessel is meant to be substantially horizontal or at a slight tilt as shown in the drawings of FIG. 2 and 3, so that the investment tends to flow on the lip 22 and into the vessel through opening 14.

While filling with investment material 4, the mold 10 is vibrated in a horizontal position for ensuring proper settling of the investment material 4. The reduced opening 14 between cap 20 and mold 10 prevents excess investment material 4 from being forced into the mold 10 and ensures that the mold 10 is filled at a rate which does not entrap air bubbles. The horizontal positioning of the mold 10 ensures that each coping pattern 7 is filled at an efficient position so that the side wall of the coping pattern 7 is filled first which allows the investment material 4 to move up to the occlusal surface of the coping pattern 7 and finally, over the side wall of the coping 7.

Any bubbles remaining in the investment material 4 are dissipated as the investment material 4 travels over lip 22 and the inclined surface of wedge 25.

Once the mold 10 is filled with investment material 4, the mold 10 is returned to an upright position; and the cap 20 is removed.

The cap 20 allows for numerous molds to be filled from the same mixture of investment material 4, i.e. within the setting time limit for the investment material 4. According to the present invention, the cap 20 permits more molds to be formed then were possible with the known devices, for instance, three molds in six minutes.

While specific embodiments of the invention have been shown and described in detail to illustrate the application of the principles of the invention, it will be understood that the invention may be embodied otherwise without departing from such principles.

What is claimed is:

1. A cap for a vessel which receives an investment material, the vessel having a wall, an open top and an inner edge at the open top, the cap comprising:

a platform having a contoured edge and having an underside, the cap being removably engageable with the open top of the vessel;

a portion on the underside of the platform frictionally engageable with at least a portion of the inner edge of the vessel;

the contoured edge of the platform and the inner edge of the vessel defining an opening for receiving the investment material when the platform is placed over the open top; and a lip on the platform at the contoured edge for channeling the investment material to the opening.

2. The cap according to claim 1, wherein the portion is a wedge and includes a front end and a back end.

3. The cap according to claim 2, wherein the wedge further includes an outer surface slightly inclined from the front end to the back end.

4. The cap according to claim 3, wherein the back end of the wedge is frictionally engageable with the wall of the vessel.

5. The cap according to claim 4, wherein the front end of the wedge is located at the contoured edge of the platform.

6. The cap according to claim 5, wherein the lip outwardly extends from the platform.

7. The cap according to claim 6, wherein the contoured edge of the platform has a semi-circular shape.

8. The cap according to claim 7, wherein the front end of the wedge has a semi-circular profile in direct alignment with the contoured edge.

9. The cap according to claim 1, wherein the lip includes a slightly inclined surface leading to the contoured edge of the platform.

10. The cap according to claim 8, wherein the lip has a semi-circular cross-section.

11. The cap according to claim 10, wherein the lip includes a slightly inclined surface leading to the contoured edge of the platform.

12. The cap according to claim 11, wherein the portion comprises a wedge which has a substantially oblong-shaped cross-section.

13. The cap according to claim 3, wherein an upper side of platform and the wedge have a depression therein.

14. The cap according to claim 13, wherein the depression includes a front wall and a rear wall.

15. The cap according to claim 14, wherein the depression further includes a depth which gradually increases from the front wall to the rear wall.

16. The cap according to claim 15, wherein the cap is made of a thermoplastic material.

17. The cap according to claim 16, wherein the thermoplastic material is transparent.

18. A combination vessel and cap for receiving an investment material for precision lost wax casting, comprising:

a vessel having a side wall, an open top and an inner edge at the open top, the vessel having a bottom and a sprue forming structure connected to the bottom and extending to a volume of the vessel;

a cap for partially closing the open top of the vessel, particularly when the vessel is in a horizontal position for receiving investment material into the vessel, the cap comprising a platform having means for retaining the platform to the open top, the platform having a recess at one edge forming an opening into the open top; and a lip around the recess for channeling investment material poured onto the lip into the opening.

19. A combination of claim 18, including a depending portion connected to the platform and extending to the open top and in frictional engagement with the inner edge for frictionally holding the cap to the vessel.

\* \* \* \* \*